US011570998B2

(12) United States Patent
Pfanstiel et al.

(10) Patent No.: US 11,570,998 B2
(45) Date of Patent: Feb. 7, 2023

(54) DETERMINING THE THICKNESS PROFILE OF WORK PRODUCTS

(71) Applicant: John Bean Technologies Corporation, Chicago, IL (US)

(72) Inventors: David Pfanstiel, Canton, GA (US); Daniel Holmes, Atlanta, GA (US); Richard D. Stockard, Kirkland, WA (US); Arthur W. Vogeley, Jr., Lynnwood, WA (US)

(73) Assignee: John Bean Technologies Corporation, Chicago, IL (US)

( * ) Notice: Subject to any disclaimer, the term of this patent is extended or adjusted under 35 U.S.C. 154(b) by 398 days.

(21) Appl. No.: 16/887,057

(22) Filed: May 29, 2020

(65) Prior Publication Data

US 2020/0375203 A1 Dec. 3, 2020

Related U.S. Application Data

(60) Provisional application No. 62/855,700, filed on May 31, 2019.

(51) Int. Cl.
*A22C 17/00* (2006.01)
*G06T 7/62* (2017.01)
(Continued)

(52) U.S. Cl.
CPC .......... *A22C 17/0086* (2013.01); *B26D 5/007* (2013.01); *B26D 7/0625* (2013.01);
(Continued)

(58) Field of Classification Search
CPC ..... A22C 17/0086; G06T 7/62; G06T 7/0004; G06T 2207/10116; G06T 2207/30128;
(Continued)

(56) References Cited

U.S. PATENT DOCUMENTS 4,875,254 A 10/1989 Rudy et al.
4,962,568 A 10/1990 Rudy et al.
(Continued)

FOREIGN PATENT DOCUMENTS

WO 2017/093539 A1 6/2017

OTHER PUBLICATIONS

International Search Report and Written Opinion dated Sep. 18, 2020, issued in corresponding International Application No. PCT/US2020/034889, filed May 28, 2020, 12 pages.

*Primary Examiner* — Omar H Nixon
(74) *Attorney, Agent, or Firm* — Christensen O'Connor Johnson Kindness PLLC

(57) ABSTRACT

A processing system (10) and a corresponding method are provided for processing work products (WP), including food items, to locate and quantify voids, undercuts and similar anomalies in the work products. The work products are conveyed past an X-ray scanner (14) by a conveyance device (12). Data from the X-ray scanning is transmitted to control system (18). Simultaneously with the X-ray scanning of the work product, the work product is optically scanned at the same location on the work product where X-ray scanning is occurring. The data from the optical scanner is also transmitted to the control system. Such data is analyzed to develop or generate the thickness profile of the work product. From the differences in the thickness profiles generated from the X-ray scanning data versus the optical scanning data, the location of voids, undercuts and similar anomalies can be determined by the control system. This information is used by the processing system (10) to process the work product as desired, including adjusting for the locations and sizes of voids, undercuts and similar anomalies present in the work product.

20 Claims, 9 Drawing Sheets

(51) Int. Cl.

| | | |
|---|---|---|
| | *B26D 5/00* | (2006.01) |
| | *B26D 7/06* | (2006.01) |
| | *B26F 3/00* | (2006.01) |
| | *G01B 11/06* | (2006.01) |
| | *G01B 15/02* | (2006.01) |
| | *G01N 23/083* | (2018.01) |
| | *G01N 33/12* | (2006.01) |
| | *G06T 7/00* | (2017.01) |

(52) U.S. Cl.
CPC .............. *B26F 3/004* (2013.01); *G01B 11/06* (2013.01); *G01B 15/02* (2013.01); *G01N 23/083* (2013.01); *G01N 33/12* (2013.01); *G06T 7/0004* (2013.01); *G06T 7/62* (2017.01); *B26D 2210/02* (2013.01); *G06T 2207/10116* (2013.01); *G06T 2207/30128* (2013.01)

(58) Field of Classification Search
CPC .. B26D 5/007; B26D 7/0625; B26D 2210/02; B26F 3/004; G01B 11/06; G01B 15/02; G01N 23/083; G01N 33/12
USPC ........................................................ 356/630
See application file for complete search history.

(56) References Cited

U.S. PATENT DOCUMENTS

| | | |
|---|---|---|
| 5,585,603 A | 12/1996 | Vogeley, Jr. |
| 5,868,056 A | 2/1999 | Pfarr et al. |
| 5,960,104 A | 9/1999 | Conners et al. |
| 6,854,590 B2 | 2/2005 | Rudy et al. |
| 2009/0080706 A1 | 3/2009 | Tao et al. |
| 2018/0029246 A1* | 2/2018 | Blaine ..................... B26D 7/30 |

* cited by examiner

X Y TRANSLATION

ROTATION

SCALE Y

SCALE X

SHEAR X

SHEAR Y

DETERMINING THE THICKNESS PROFILE OF WORK PRODUCTS

CROSS-REFERENCE TO RELATED APPLICATION

This application claims the benefit of U.S. Provisional Application No. 62/855,700, filed May 31, 2019, the entire contents of which are incorporated herein by reference in their entirety.

BACKGROUND

Work products, including food products, are portioned or otherwise cut into smaller portions by processors in accordance with customer needs. Customers usually desire to portion and/or trim the work products into uniform sizes, for example, steaks to be served in restaurants, chicken fillets used in frozen dinners or in chicken burgers or bacon slabs cut from pork bellies. Much of the portioning/trimming of work products, in particular food products, is now carried out with the use of high-speed portioning machines. These machines rely on various scanning techniques to ascertain the size and shape of the food product as they are being advanced on a moving conveyor. This information is analyzed with the aid of a computer to determine how to most efficiently cut the food product into optimum sizes or portions. For example, a customer may desire bacon portioned into one-pound slabs or may desire chicken breast portions in two different weight sizes, but with no fat or with a limited amount of acceptable fat. The pork belly or chicken breast is scanned as it moves on an infeed conveyor belt and a determination is made through the use of a computer as how to best portion the pork belly or chicken breast to achieve the weight(s) desired by the customer, so as to use the pork belly or chicken breast most effectively.

Cutting and/or trimming of the work product can be carried out by various cutting devices, including high-speed liquid jet cutters, wherein the liquid may include, for example, water or liquid nitrogen. Alternatively, the cutting device may be composed of a rotary or reciprocating blade. Once the cutting/trimming has occurred, the resulting portions are off-loaded from the cutting conveyor and placed on a takeaway conveyor for further processing or perhaps to be placed in a storage bin.

Portioning machines of the foregoing type are known in the art. Such portioning machines, or portions thereof, are disclosed in prior patents, for example, U.S. Pat. Nos. 4,962,568 and 5,868,056, which are incorporated by reference herein. Typically, the work products are first carried by an infeed conveyor past the scanning station where at the work products are scanned to ascertain selected physical parameters, for example, the size and shape, including length, width and/or thickness profile. From this information, the weight of the work product, or portions thereof, can be determined by utilizing an assumed density for the work product.

The scanning of the work product can be carried out utilizing a variety of techniques, including X-ray scanning and optical scanning. In X-ray scanning, X-rays are passed through the work product, with the level of attenuation of the work product being related to mass of the work product. An optical scanning system may utilize a CCD camera or video camera to view a work product illuminated by one or more light sources. The optical camera is capable of determining the physical parameters of the overall exterior configuration of the work product, including its size and shape. These scanning techniques assume that the bottom of the work product lies flat on the conveyor on which the work product is being carried during scanning and subsequent trimming or cutting. However, the bottom side of the work product may not lie flat against the top surface of the conveyor belt, rather an undercut may exist beneath the work product. Also, an unseen void may exist within the interior of the work product. If these situations exist, then in typical scanning systems the undercut or void is not detected. Accordingly, the work product is analyzed as if the undercut or void did not exist. As such, erroneous information is utilized concerning the physical parameters of the work product. If the goal is to cut the work product into uniform portions by weight, then the presence of an undercut or void can cause the end portion to not be within the approved weight range for the portion(s) cut from the work product.

X-ray scanners can "see through" work products, including foods. However, X-ray scanners cannot detect undercuts or voids. Also, optical scanners are capable of ascertaining the physical aspects of the exterior of the work product, but are not able to ascertain the existence of a void within the work product or an undercut beneath the work product.

The present disclosure seeks to provide a method and system for locating voids, undercuts and similar anomalies in the work product and then analyzing the work product taking into consideration the existence of voids, undercuts or other anomalies so as to portion or otherwise process the work product knowing the existence, location, size and shape of any voids, undercuts or similar anomalies in the work product.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

An embodiment of the present disclosure includes a method for determining the thickness profile of a work product, comprising (a) scanning a work product with an X-ray scanner, (b) analyzing the data from the X-ray scanner with a computer processor to develop a thickness profile of the work product, (c) scanning the work product with an optical scanner, (d) analyzing the data from the optical scanner with a computer processor to develop a thickness profile of the work product based on the optical scanning data, (e) comparing the thickness profiles from the X-ray scanning data and the optical scanning data and determining (quantifying) the differences between the thickness profiles from the X-ray scanning data and the optical scanning data, and (f) mapping the location(s) on the work product where a difference exists between the thickness profiles from the X-ray scanning data and the optical scanning data.

The method of any embodiment of the present disclosure, wherein the differences between the thickness profiles from the X-ray scanning data and the optical scanning data correspond to voids, undercuts and similar locations associated with the work product that is not occupied by the work product.

The method of any embodiment of the present disclosure, wherein the work product is a food product, and the differences between the thickness profile developed from the X-ray scanning data and the thickness profile developed from the optical scanning data correspond to a void in the work product, an undercut beneath the work product, or other location devoid of the work product.

The method of any embodiment of the present disclosure, wherein the food product comprises meat, and the difference between the thickness profile from the X-ray scanning relative to the thickness profile from the optical scanning comprises a void in the meat, an undercut in the lower surface of the mat, or other location that is devoid of the meat.

The method of any embodiment of the present disclosure, further comprising transporting the work product on a conveyance device past the X-ray scanner and the optical scanner.

The method of any embodiment of the present disclosure, further comprising positioning the X-ray scanner and the optical scanner relative to the conveyance device.

The method of any embodiment of the present disclosure, further comprising positioning the X-ray scanner and the optical scanner to simultaneously scan the same location on the work product.

The method of any embodiment of the present disclosure, further comprising processing the work product using the determined differences between the thickness profiles from the X-ray scanning data and the optical scanning data and the location(s) on the work product where a difference exists between the thickness profiles from the X-ray scanning data and the optical scanning data.

The method of any embodiment of the present disclosure, wherein the work product is processed by trimming, cutting or portioning.

The method of any embodiment of the present disclosure, further comprising transporting the work product in a direction of travel past the X-ray scanner and the optical scanner.

The method of any embodiment of the present disclosure, wherein the X-ray scanner scans the work product along a line extending transversely to the direction of travel of the work product.

The method of any embodiment of the present disclosure, wherein the optical scanner scans the work product along a line extending transversely to the direction of travel of the work product.

The method of any embodiment of the present disclosure, wherein the optical scanner scans the work product along the same line that the X-ray scanner scans the work product.

The method of any embodiment of the present disclosure, wherein the conveyance device comprises a first conveyor corresponding to the X-ray scanner and a second conveyor corresponding to the optical scanner.

The method of any embodiment of the present disclosure, further comprising (g) wherein the data from the X-ray scanning comprises a first data set corresponding to the two dimensional shape of the work product, (h) wherein the data set from the optical scanning comprises a second data set corresponding to the two dimensional shape of the work product, (i) comparing the first and second data sets from the X-ray scanning and the optical scanning corresponding to the two-dimensional shape of the work product, and (j) determining if a sufficient variation exists between the first and second data sets to require translation of the first data set into the second data set.

The method of any embodiment of the present disclosure, wherein translation of the first data set from the X-ray scanning onto the second data set from the optical scanning comprises one or more of: (i) directional translation of the work product; (ii) rotational translation of the work product; (iii) scaling the size of the work product; (iv) shear distortion of the work product.

The method of any embodiment of the present disclosure, wherein the conveyance device comprises a first conveyor corresponding to the locations of the X-ray scanner and the optical scanner; and further comprising a second optical scanner and a second conveyor corresponding to the location of the second optical scanner.

The method of any embodiment of the present disclosure, wherein the data set from the optical scanner comprises a second data set corresponding to the two-dimensional shape of the work product, wherein the data from the second optical scanner comprises a third data set corresponding to the two-dimensional shape of the work product, and further comprising comparing the second and third data sets from the optical scanner and from the second optical scanner corresponding to the two-dimensional shape of the work product, and determining that sufficient variation exists between the second and third data sets to require a translation of the second data set into the third data set.

The method of any embodiment of the present disclosure, wherein translation of the second data set into the third data set comprises one or more of: directional translation of the work product; rotational translation of the work product; scaling of the size of the work product; shear distortion of the work product.

The method of any embodiment of the present disclosure, wherein the conveyance device comprised a first conveyor corresponding to the X-ray scanner and the optical scanner and a second conveyor corresponding to a processing station whereat the work product is processed using the thickness profiles determined from the X-ray scanning data and the optical scanning data.

A further embodiment of the present disclosure including a system for determining the thickness profile of a work product, comprising: a conveyance device for conveying the work product; an X-ray scanner for scanning the work product being conveyed on the conveyance device and generating a first data set regarding the physical characteristics of the work product, including a thickness profile of the work product; an optical scanner for scanning the work product being conveyed on the conveyance device for generating a second data set regarding the physical characteristics of the work product, including the thickness profile of the work product; and a control system configured to: generating thickness profiles of the work product from the X-ray scanning data and the optical scanning data; quantifying the differences between the thickness profiles of the work product from the X-ray scanning data and the optical scanning data; and mapping the location(s) on the work product where differences exist between the thickness profiles from the X-ray scanning data and the optical scanning data.

The system of any embodiment of the present disclosure, wherein the difference between the thickness profiles of the work product from the X-ray scanning data and the optical scanning data corresponds to a void in the work product, an undercut beneath the work product, or other location with respect to the work product that is devoid of the work product.

The system of any embodiment of the present disclosure, wherein the work product comprises a food product and the differences between the thickness profile of the food product from the X-ray scanning data and the thickness profile of the food product from the optical scanning data corresponds to a void in the food product, an undercut beneath the food product, or location with respect to the food product that is devoid of the food product.

The system of any embodiment of the present disclosure, wherein the food product is meat, and the difference between the thickness profile of the meat from the X-ray scanning relative to the thickness profile of the meat from the optical scanning is due to the presence of a void within the meat, an undercut beneath the meat, or other location with respect to the meat that is devoid of meat.

The system of any embodiment of the present disclosure, wherein the X-ray scanner and the optical scanner are positioned relative to the conveyance device to simultaneously scan the same location on the work product.

The system of any embodiment of the present disclosure, wherein the X-ray scanner is configured to scan the work product along a line extending transversely to the direction of travel of the work product on the conveyance device.

The system of any embodiment of the present disclosure, wherein the optical scanner is configured to scan the work product along a line extending transversely to the direction of travel of the work product on the conveyance device.

The system of any embodiment of the present disclosure, wherein the optical scanner is configured to scan the work product along the same line that the X-ray scanner is configured to scan the work product.

The system of any embodiment of the present disclosure, wherein the optical scanner is configured to scan the work product along the same line and at the same time that the X-ray scanner is configured to scan the work product.

The system of any embodiment of the present disclosure, wherein the conveyance device comprises a first conveyor corresponding to the X-ray scanner and a second conveyor corresponding to the optical scanner.

The system of any embodiment of the present disclosure, wherein the control system compares a first data set from the X-ray scanning data corresponding to the two-dimensional shape of the work product with a second data set from the optical data scanning corresponding to the two-dimensional shape of the work product and comparing the first and second data sets from the X-ray scanning and the optical scanning to determine if a sufficient variation exists between the first and second data sets to require translation of the first data set into the second data set.

The system of any embodiment of the present disclosure, wherein the translation of the first data set from the X-ray scanning into the second data set from the optical scanning comprises one or more of: directional translation of the work product; rotational translation of the work product; scaling of the size of the work product; and shear distortion of the work product.

The system of any embodiment of the present disclosure, further comprising a processing station located downstream of the optical scanner for processing the work product using the quantified differences between the thickness profile of the work product from the X-ray scanning versus the thickness profile of the work product from the optical scanning.

The system of any embodiment of the present disclosure, wherein the processing station comprises a cutter for trimming, cutting, and/or portioning the work product.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
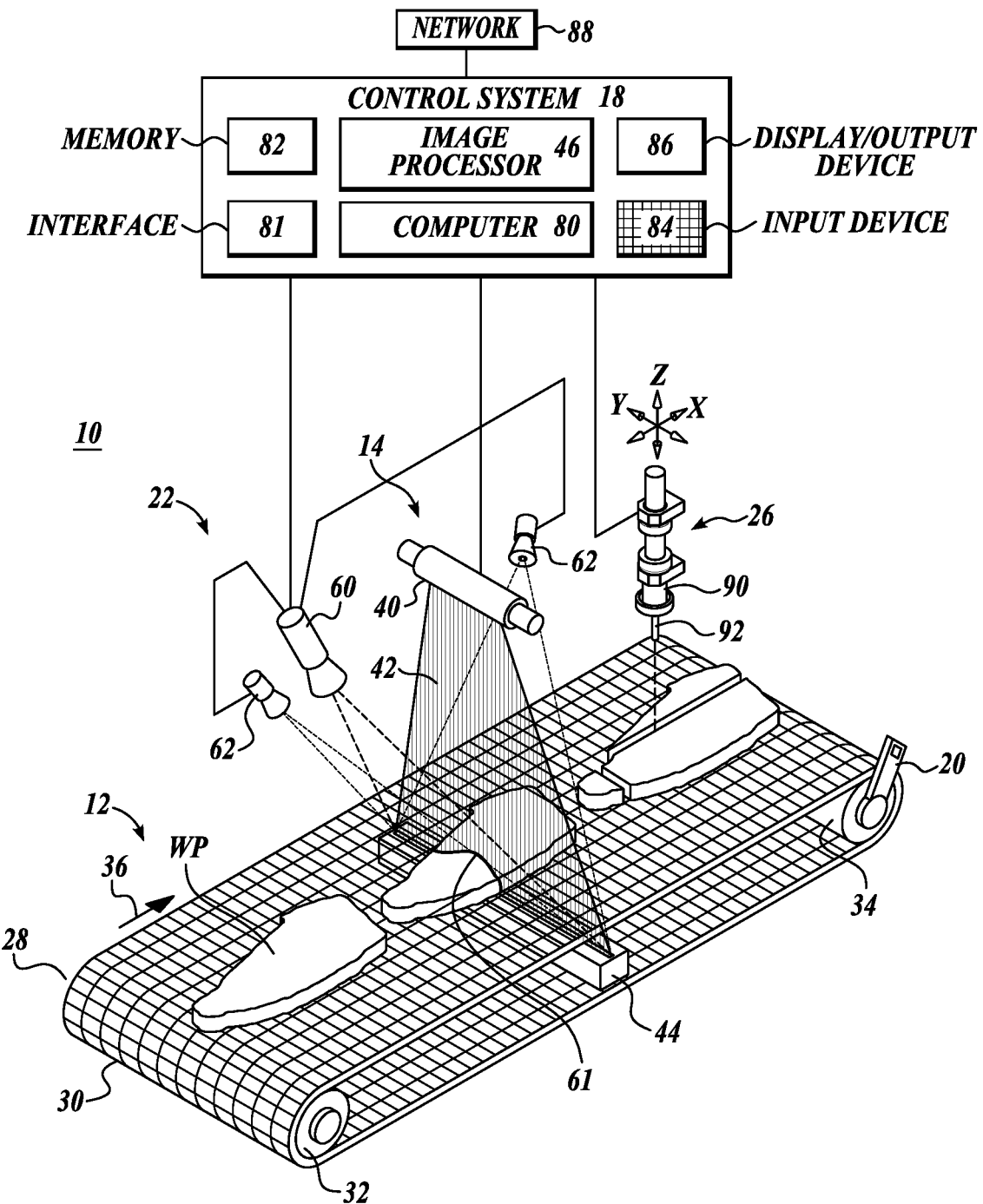
FIG. 1 is a schematic representation of a system and apparatus for processing work products according to a first embodiment of the present disclosure.

The description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to "directions," such as "forward," "rearward," "front," "back," "ahead," "behind," "upward," "downward," "above," "below," "top," "bottom," "right hand," "left hand," "in," "out," "extended," "advanced," "retracted," "proximal," and "distal." These references and other similar references in the present application are only to assist in helping describe and understand the present disclosure and are not intended to limit the present invention to these directions.

The present application may include modifiers such as the words "generally," "approximately," "about", or "substantially." These terms are meant to serve as modifiers to indicate that the "dimension," "shape," "temperature,"

"time," "quantity," "percentage," or other physical parameter in question need not be exact, but may vary as long as the function that is required to be performed can be carried out. For example, in the phrase "generally circular in shape," the shape need not be exactly circular as long as the required function of the structure in question can be carried out.

In the following description, various embodiments of the present disclosure are described. In the following description and in the accompanying drawings, the corresponding systems assemblies, apparatus and units may be identified by the same part number, but with an alpha suffix or a prime or double prime designation. The descriptions of the parts/components of such systems assemblies, apparatus, and units that are the same or similar are not repeated so as to avoid redundancy in the present application.

In the present application, references to "food," "food products," "food pieces," and "food items," are used interchangeably.

System Summary

An embodiment of the processing system 10 of the present disclosure is illustrated in FIG. 1 as including, in basic form, the conveyance device 12 in a form of a conveyor 28 having an endless belt 30 for carrying work products or workpiece WP, such as food products, for example, pork bellies, poultry breasts and other types of food products, past an X-ray scanner 14 to ascertain physical parameters of the work product. Such physical parameters may include the size and/or shape of the work product including, for example, the length, the width, aspect ratio, thickness, thickness profile, contour, outer contour, outer perimeter, outer perimeter shape, volume and/or weight of the work product. With respect to the thickness profile of the work product, such profile can be ascertained along the length of the work product, across the width of the work product as well as both across the width and along the length of the work product. The data from the X-ray scanner 14 is transmitted to control system 18. Such data is coordinated with corresponding data from an encoder 20 associated with the conveyance device 12 so as to match the X-ray scanning data with positions along the conveyance device corresponding to locations along the work product being scanned.

The system 10 also includes an optical scanner 22 which is positioned relative to the conveyance device 12 to simultaneously scan the work produce with the X-ray scanning being conducted. The optical scanner also ascertains physical parameters of the work product, including, for example, physical parameters pertaining to the size and/or shape of the work product as discussed above with respect to the X-ray scanner 14. The data from the optical scanning is also transmitted to the control system 18 and can be used to develop a thickness profile of the work product.

The thickness profile of the work product determined from the X-ray scanner is based on the mass of the work product. Thus, if there is a void within the work product or an undercut at the bottom of the work product, this can be ascertained by the X-ray scanner due to the reduction in mass resulting from the void or undercut. However, the optical scanner ascertains the height and contours of the top exterior of the work product and does not take into consideration whether there is a void within the work product or an undercut beneath the work product. As such, the two thickness profiles generated by the X-ray scanning and the optical scanning can be compared. If a void exists within the work product or an undercut exists beneath the work product, the thickness of the work product as determined by the optical scanning will be larger than the thickness of the work product as determined from the X-ray scanning With this information, it is possible for the control system 18 to not only ascertain the existence of a void or undercut, but also more specifically the shape, size, and location of the void or undercut. This information can be used by the control system 18 in determining how to trim, cut and/or portion the work product into desired final pieces, for example, final pieces of a desired weight or weight range.

The need for mapping of the thickness data ascertained from the X-ray scanning with the thickness data ascertained from optical scanning can be reduced or perhaps eliminated if the X-ray scanner and optical scanner are configured to simultaneously scan the same location(s) of the work product.

Even if there still be a need for mapping thickness data from the X-ray and optical scanning operations, if the scanning occurs simultaneously, the matching or mapping of the data will likely be more accurate. Also, the matching/matting may possibly be done with simple timestamps, and not with any need for monitoring of the position of the work pieces on the belt with encoder "counts" or other monitoring techniques.

The work product can be trimmed or cut at a cutting station 26 using one or more cutters controlled by control systems 18. Thereafter, the trimmed or cut work product may be transferred on for other or further processing. Other types of processing in addition to or in lieu of the cutting or trimming of the work product can occur using the information regarding the thickness profile of the work product ascertained using the data from the X-ray scanner 14 and the optical scanner 22.

Conveyor

Next, describing the foregoing aspects of the processing system 10 in more detail, referring to FIG. 1, conveyance device 12 is in the form of a belt conveyor 28 having an endless belt 30 trained over end rollers 32 and 34. The encoder 20 is associated with the end roller 34. The roller 34 is powered so as to drive the conveyor belt in the downstream direction as shown by arrow 36 past the X-ray scanner 14, optical scanner 22, and cutting station 26. As noted above, the encoder 20 monitors the location or position of the belt 30 along the length of the conveyor 28.

The belt 30 is illustrated as being of open form or grid construction so that the water jet(s) at the cutting station 26 is (are) free to pass downwardly through the belt to a collection tank or other receptacle, not shown, positioned beneath the conveyance device. Various constructs of conveyor belts corresponding to belt 30 are described in U.S. Pat. No. 6,854,590, incorporated by reference herein.

X-Ray Scanning

X-ray scanner 14 is used to inspect the work product WP to determine physical parameters of the work product, including as described above, the shape and size of the work product and further including, for example, the thickness and thickness profile of the work product. The X-ray scanner can also determine if undesirable material, such as bones, fat, metal, plastic, glass, is located within the work product.

Generally, X-rays are attenuated as they pass through an object in proportion to the total mass of the material to which the X-rays pass. The intensity of the X-rays received by an X-ray detector, after they have passed through the object such as work product WP, is inversely proportional to the total mass of the object. For example, X-rays passing through a work product that has a void or an undercut will be less attenuated as X-rays that pass through the work product without an undercut or void. Thus, the portion of a work product at which a void or undercut is located will be analyzed as being of lesser thickness than adjacent the sections of the work product without an undercut or void.

Further, using a given value for the density of the work product being analyzed, whether beef, poultry or fish, the dimensional thickness of the work product can be calculated. This information can be determined for the entire volume of the work product. A general description of the nature and use of X-rays in processing food products can be found in U.S. Pat. No. 5,585,603, incorporated herein by reference.

As noted above, system 10 includes a position sensor in the form of encoder 20 that generates a signal indicative of the position of the belt 30, and thus the work product WP, along the length of the conveyor 28. As the work products move along the conveyor 28, with respect to X-ray scanner 14 the position of the work product along the length and width of the conveyor belt 30 can be ascertained by the X-ray system. As noted above, the X-ray scanner can also provide other information with respect to the physical parameters of the work product in addition to the thickness or the thickness profile of the work product described above. Such physical parameters include, for example, the length, width, aspect ratio, contour, outer contour configuration, perimeter, outer perimeter configuration, outer perimeter size and/or shape, volume and/or weight of the work product. With respect to the outer perimeter configuration of the work product, the X-ray scanner can be used to determine locations along the outer perimeter of the work product, including based on an X-Y coordinate system or other coordinate system.

The X-ray scanner 14 includes an X-ray source or generator 40 for emitting X-rays 42 downwardly toward the work product. An X-ray detector 44 is located beneath the upper run of the conveyor belt 30 for receiving the X-rays 42 that have passed through the work product. The X-ray detector 44 includes a linear array of detector units extending across the underside of the conveyor belt 30 to generate a signal corresponding to the intensity of the X-rays impinging thereon. The signals generated by the X-ray detector 44 are transmitted to an image processor 46, which forms part of the overall control system 18. The control system processes the data signals from the X-ray detector 44 to determine physical parameters of the work product, including the thickness profile of the work product, across the width of the work product as well as along the length of the work product. As noted above, the physical parameters ascertainable from the X-ray scanning also includes the shape and size of the work product as well as the location of the work product on the conveyor belt 20.

Figure 2:
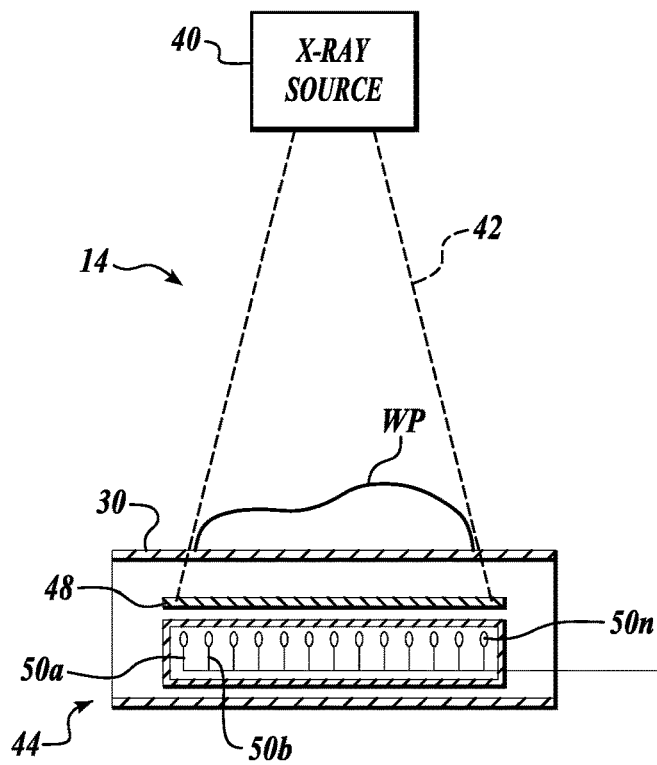
FIG. 2 is a schematic view of an X-ray scanner which may be utilized in the system and method of the present disclosure.

Referring to FIG. 2, an X-ray detector 14 is illustrated as including a layer or strip of scintillator material 48 located above a plurality of photodiodes 50a-50n. The X-ray source or generator 40 is located a sufficient distance above the conveyor belt 30 so that the X-rays 42 emitted from the generator 40 completely encompass the length of the X-ray detector 44 that extends across the conveyor belt 30. The X-rays 42 pass through the work product WP, through the upper run of the conveyor belt 30, and then impinge upon the layer or strip of scintillator material 48. Since the photodiodes 50a-50n respond only to visible light, the scintillator material 48 is used to convert the X-ray energy impinging thereon into visible light flashes that are proportional to the strength of the received X-rays. The photodiodes 50a-50n generate electrical signals that have an amplitude proportional to the intensity of the light received from the scintillator material 48. These electrical signals are relayed to the image processor 46.

As shown in FIG. 1, the photodiodes 50a-50n are arranged in a line across the width of the conveyor belt 30 for detecting X-rays passing through a line or "slice" of the work product WP. Alternative photodiode layouts are possible, for example, the photodiodes can be positioned in several rows to form a rectangular grid thereby to increase the scanning area of the X-ray detector 44, if desired.

Figure 3:
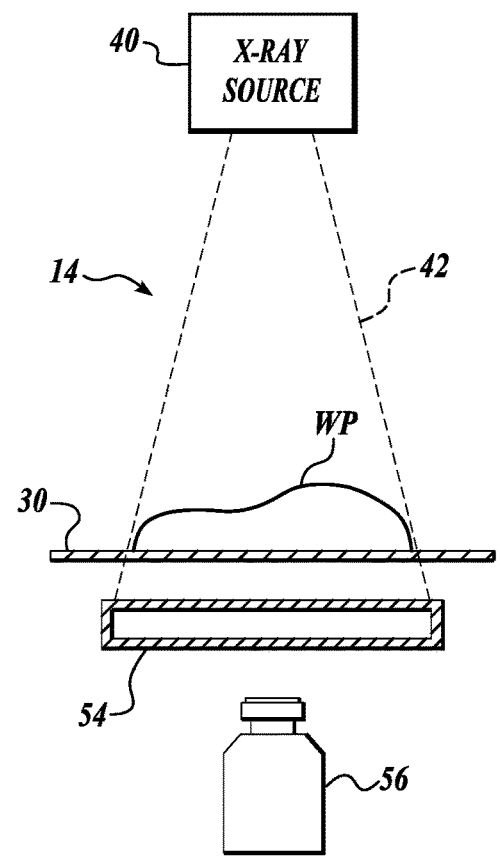
FIG. 3 is a schematic view of another X-ray scanner that may be utilized with the system and method of the present disclosure.

Other embodiments of an X-ray scanner can be utilized, which are also capable of detecting the intensity (or attenuation) of the X-rays that have passed through the work product WP to determine a thickness profile of the work product. For example, referring to FIG. 3, an alternative embodiment of an X-ray detector 14' includes a fluoroscope screen 54. The screen is activated to produce light flashes in proportion to the attenuation of the impinging X-rays 42. Light flashes are then recorded by a video camera 56, or other device capable of capturing the "picture" produced by the fluoroscope screen 54. The images captured by the video camera 56 are transmitted to image processor 46 and converted into digital values related to the intensity of the light generated by the fluoroscope screen 54.

Further alternatively, direct flat panel X-ray imaging technology or direct radiography may be used. For example, an array of amorphous selenium detectors may be used as an X-ray detector to directly detect the intensity of the impinging X-rays, and to transmit data in this regard to the image processor 46.

Other X-ray options include the use of a dual-energy X-ray source or the photon-counting, multi-bin X-ray system.

Further, other types of scanners may be employed, for example, infrared scanning, sonar/ultrasound scanning, CT scanning or MRI scanning Optical Scanning Referring to FIG. 1, optical scanner 22 is positioned along conveyance system 12. Optical scanning can be carried out using a variety of techniques, including with a scanner such as scanner 22, to view a work product WP illuminated by one or more light sources 60. The light from the light source(s) 60 is extended across the moving conveyor belt 30 to define a sharp shadow or light stripe 61, with the area forward of the transverse beam being dark. When no work product is being carried by the conveyor belt 30, the shadow line/light stripe 61 forms a straight line across the belt 30. However, when a work product WP passes across the shadow line/light stripe, the upper irregular surface of the work product produces an irregular shadow line/light stripe as viewed by video cameras 62 directed downwardly on the work product and the shadow line/light stripe 61. The video cameras detect the displacement of the shadow line/light stripe 61 (i.e., in the Z-axis direction) from the position it would occupy if no work product is present on the conveyor belt 30. This upward displacement of the light stripe 61 represents the "thickness" of the work product along the shadow line/light stripe as viewed by the optical scanner.

The length of the work product is determined by the length of time that the shadow lines 61 are created by the work product. In this regard, encoder 20 generates pulses at fixed time intervals corresponding to the forward movement of the conveyor belt 30. During such movement of the conveyor belt, the thickness profile of the entire work product in both the "X" and the "Y" direction relative to the conveyor belt is generated.

As shown in FIG. 1, the light source 60 and video cameras 62 are positioned relative to the X-ray scanner 14 so that the light stripe 61 coincides with and is aligned with the X-ray detector 44 positioned across the conveyor belt 30. As such, the X-ray scanner and the optical scanner simultaneously scan the same transverse location (slice) across the work product. This alignment of the light stripe 61 with the X-ray detector 44 may eliminate the need for transformation of the data from the X-ray scanner 14 with the data from the optical scanner 22 due to the work pieces moving or shifting. Though mapping of the data from the X-ray scanner to the data from the optical scanner may be required due to the somewhat different viewpoints for the X-ray detector and the optical cameras or during calibration or set up of the processing system 10.

Although a single light source 60 is shown in FIGURES, multiple light sources can be utilized. For example, a second light source may be positioned on the opposite side of X-ray generator 40 from the light source 60.

Also, although two cameras 62 are shown as in use in FIG. 1, a single camera can be used. However, "shadowing" can occur if a single camera is used. In this regard, the light stripe may be momentarily blocked from view of the single camera by a section of the workpiece that extends upward above the surrounding portions of the work piece. This may not be a problem or source of inaccuracy. But if shadowing results in missing height data, the X-ray image data would be used to fill in the missing data.

Further, as noted above, the processing system 10 is designed to ascertain whether or not there is a void in the work product WP or whether an undercut in the underside of the work product exists or whether or not the work product is lying flat on the conveyor belt 20. In this regard, as discussed above, the upward displacement of the light stripe 61 from the optical scanner provides the thickness of the work product, across the width of the work product at the location of the light stripe. However, optical scanning will not ascertain whether or not a void, undercut, etc., exists. Rather, the optical scanning instead provides the height profile of the upper surface of the work product WP relative to the top surface of the conveyor belt 30.

On the other hand, the X-ray scanning provides the actual thickness of the work product across the work product corresponding to the location of the X-ray detector. If a void, undercut or similar anomaly exists in the work product, the work product will be determined to be thinner at such location since the intensity of the X-rays passing therethrough will be greater than if no void, undercut or other anomaly exists. Thus, if the "thickness" of the work product from the optical scanning is compared with the thickness of the work product from the X-ray scanning, any different therein will indicate the presence of a void, undercut or similar anomaly causing reduced attenuation of the X-rays reaching the X-ray detector.

Figure 4A:
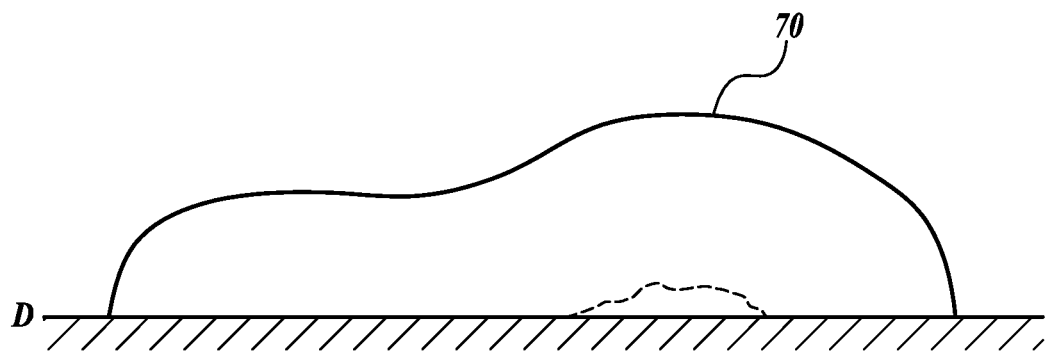
FIGS. 4A-4C are plots of thickness profiles of a work product generated by X-ray scanning and optical scanning showing the differences therebetween.
Figure 4B:
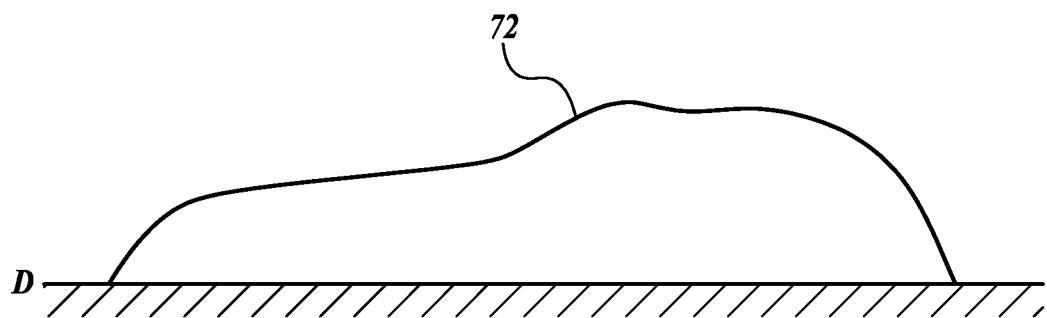
Figure 4C:
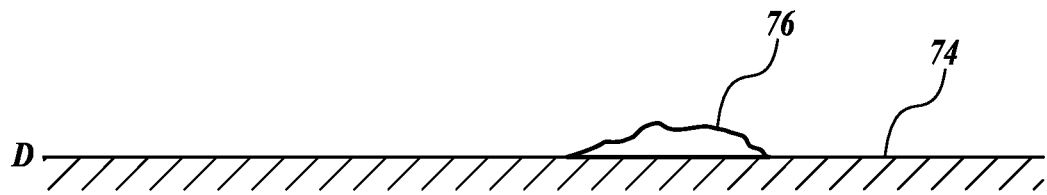

The foregoing analysis is schematically illustrated in FIGS. 4A-4C. In FIG. 4A, the profile line 70 depicts the thickness profile above the datum "D" across a "slice" of the work product as generated by optical scanner 22. The profile line 72 depicts the thickness profile above the datum "D" along the same slice of the work product as ascertained by the X-ray scanning Profile line 74 represents the height of the bottom surface work product when the X-ray height is subtracted from the optical height. For the most part, the profile line 74 is at a zero height above the datum because the height of the work product as determined by the optical scanning is the same as determined from the X-ray scanning. However, as shown in FIG. 4C, a section 76 of the profile line 74 is about the datum "D". Section 76 of the profile line 74 represents the shape, size and location of a void or undercut in the work product. Except at the location of the profile 74, the resulting height is zero relative to the datum "D". The above analysis enables the more accurate processing of the work product, for example, trimming or cutting the work product into desired portion weights.

It will be appreciated that in certain types of food products, a relatively large undercut or void can occur, especially if the food product has curled or otherwise assumed a configuration that causes a work product to not lie flat on the conveyor belt 30. For example, it is not uncommon for the edges of a smoked pork belly to turn or curl under thereby causing significant portions of the underside of the pork belly to not lie flat on the conveyor belt on which the pork belly is being supported during cutting of the pork belly into fixed weight portions. This commonly occurs along the edges of the pork belly.

Chicken breasts, especially when very fresh, can have undercutting from the edge in, or at the very front towards the back. Also, in chicken breasts when a muscle (the "tender") is removed, a hollow may occur, which is known as the "tender tunnel". This can cause inaccuracies when cutting or portioning the chicken breasts.

As discussed above, an assumed density value for the work product is used to translate the mass related data from the X-ray scanning to the height or thickness of the work product. In many situations, it will be assumed that the density value applies to the entire work product, for example, a chicken breast or fish fillet. In these situations, fat, which has less density than meat per se, is typically located around the edges of the meat. Further, the fat often is not of significant quantity, so errors caused by applying a generalized density value is typically relatively small. Further, if the fat present is on the surface of the food product is visible to the optical scanner, then the control system 18 can apply a different density value to the fat.

There are other types of food products, for example, pork bellies, that may consist of up to 50% fat, and such fat is interspersed throughout the muscle meat. In this situation, a generalized density value can be used that takes into consideration the likely level of fat in the food product.

Further, in meat food products, as indicated below, the density of fat is less than the density of the whole muscle meat. In this regard, the density of the food product being scanned can be calculated by dividing the mass measured from the X-ray scanning by the volume determined from the optical scanning. If the calculated density is less than the density of even the fat, then the conclusion is that there must be a void or undercut at the location of the food product being analyzed.

As a further matter, if it is known that the food product FP is lying flat on the conveyor belt 30, for example, if the food product has been pressed prior to scanning, then the above method for calculating density by dividing the mass determined from the X-ray scanning by the volume determination from the optical scanning can be used to determine the fat/protein muscle ratio in the food product.

For example, if the density of pork is 1.1 $g/cm^3$ and the density of fat in pork is 0.9 $g/cm^3$, if the density is calculated using the processes above as being 1.0, then pork belly being analyzed has a fat content of approximately 50%.

Figure 6:
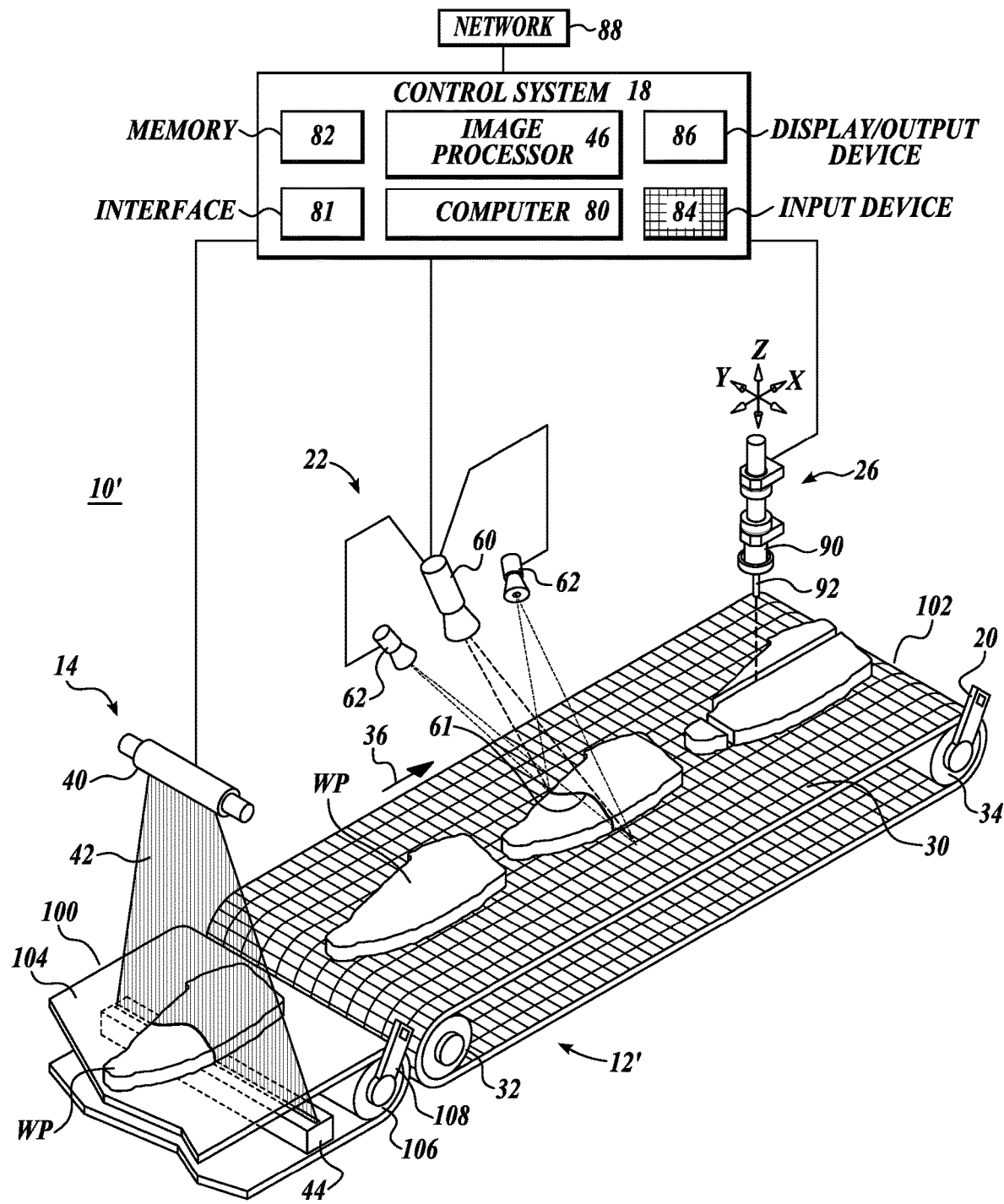
FIG. 6 is a schematic view of another embodiment of a system and apparatus for processing work products in accordance with the present disclosure.

Referring to FIG. 1, as noted above, the X-ray scanner 14 and the optical scanner 22 are positioned relative to each other so that the same "slice" across the work product is being analyzed simultaneously by the X-ray scanning and the optical scanning Although this configuration of the portioning system 10 can simplify the analysis of the X-ray scanning and the optical scanning by not requiring translation of the data from the X-ray scanning into the data of the optical scanning or vice versa, it will be appreciated that the X-ray scanner may be positioned at a different location along the conveyance device 12 than the location of the optical scanner 22, as discussed below regarding FIG. 6. In that case, it will be necessary to translate the data from the X-ray scanning into the data from the optical scanning. However, this process should be fairly straightforward in that both the X-ray scanning and optical scanning view the work product in slices across the width of the work product. The encoder data can be used to match the X-ray scanning data to the optical scanning data for the same slice location across the work product.

As noted above, the X-ray detector 44 is configured as a line array detector so as to receive X-rays along the same slice or line across the conveyor belt as the location of the light stripe 61 from the optical scanner 22. As also noted above, the X-ray detector instead can be configured as having a width along the length of the conveyor belt 20. In that situation, the data from the X-ray detector may need to be "associated" with the data from the optical scanner. In such case, the X-ray data may need to be transformed into the data from the optical scanner using existing transformation techniques.

Control System

FIG. 1 schematically illustrates control system 18 which controls the operation of processing system 10. The control system includes a computer 80 to which is operably connected the image processor 46 which receives the data from X-ray detector 44 as well as from the optical cameras 62 and processes such data for use by the computer. The control system also includes an interface 81 for receiving signals and information from encoder 20 as well as from other data sources of system 10, as described herein. A memory unit 82 is provided for storing information for use by the control system, including the computer 80. A keyboard or other input device 84 is provided to enable an operator to communicate with the control system 18. Also, a display or other output device 86 is provided to convey information from the control system, including from computer 80 to the operator. As noted below, the control system 18 controls the operation of the portioning system 10, including conveyance device 12, X-ray scanner 14, optical scanner 22, and cutting station 26. The control system 18 can be connected to a network 88. Also, rather than employing a local computer 80, a network computing system can be used for this purpose.

Cutting Devices

Once the work product has passed by the X-ray and optical scanners 14 and 22, the work product WP moves on to cutting station 26. As described above, information from the X-ray scanner and optical scanner can be combined so that locations of voids, undercuts and similar anomalies are known. With that information, the control system 18 determines how the work product can be trimmed or cut, for example, into portions of desired weights or other sizes and parameters.

Various types of cutting devices can be utilized at the cutting station 26 to cut or trim the work product as desired. One type of cutter 90 that may be used employs high-pressure water jets, as disclosed in U.S. Pat. Nos. 4,875,254, 5,365,186 and 5,868,056, incorporated herein by reference.

As schematically shown in FIG. 1, the water jet cutter 90 includes a nozzle 92 that may be moved relative to conveyor belt 30 longitudinally of the belt and laterally of the belt, as well as vertically relative to the upper surface of the belt. This enables the water jet cutter 90 to cut and/or trim the work product so as to achieve one or more desired configurations, sizes, portions, etc.

Although FIG. 1 only shows one water jet cutter 90, it is to be understood that at least several water jet cutters can be utilized in conjunction with the system 10 so as to achieve a desired production level. For example, four, eight or even more water jet cutters can be utilized in a coordinated fashion to cut and/or trim work products at cutting station 26.

Method

Figure 5:
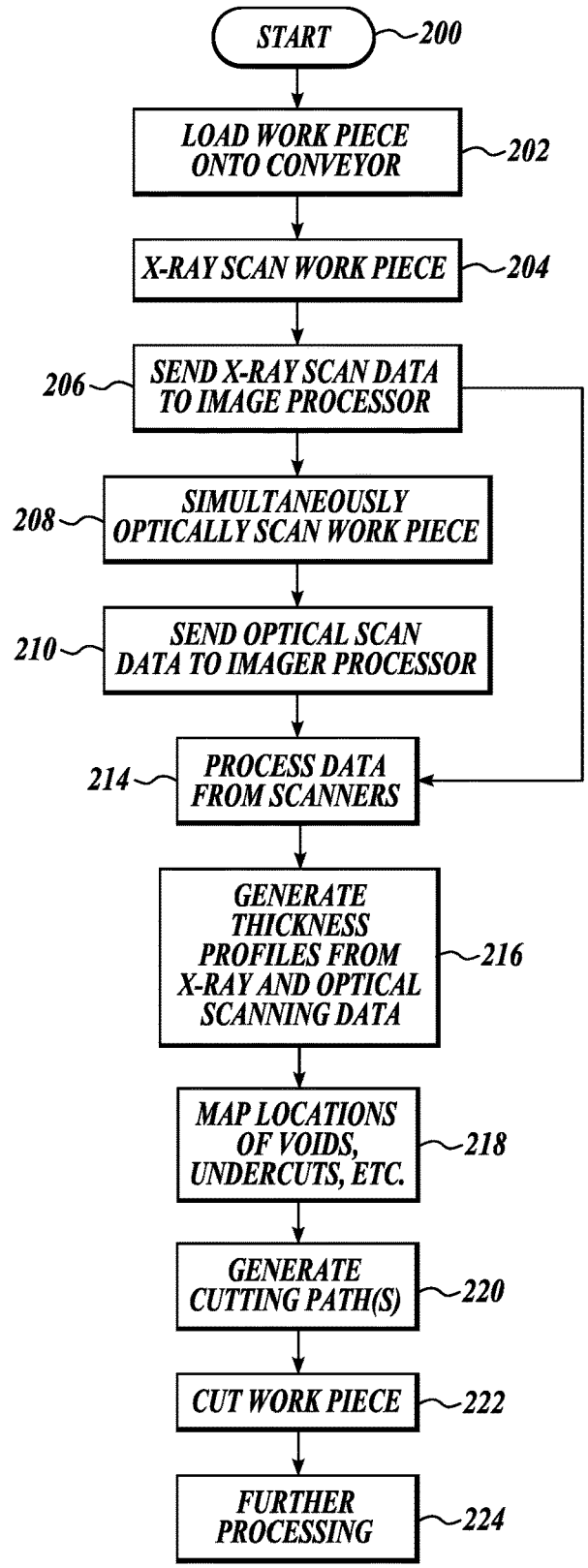
FIG. 5 is a flow diagram of a work product processing method using the system and apparatus of FIG. 1.

FIG. 5 illustrates a method of utilizing the processing system 10 of the present disclosure shown in FIGS. 1-4. The process begins at step 200 wherein work products WP are loaded onto conveyor 28 at step 202. Thereafter, the work products are scanned at step 204 using X-ray scanner 22. Next, at step 206, the data from the X-ray scanning of the work product is transmitted to image processor 46.

Thereafter, at step 208, simultaneously with the X-ray scanning of the work product, the work product is also optically scanned by scanner 22. At step 210, the data from the optical scanner is sent to the image processor 46.

Next, at step 214, the data from the X-ray scanner and optical scanner is processed with the results of such processing made available to the computer 80 so that thickness profiles from the X-ray scanning and optical scanning can be generated, at step 216. The two thickness profiles are analyzed so that the locations of voids, undercuts and similar anomalies can be mapped at step 218.

Thereafter, at step 220 the cutting path for the water jet or other type of cutter 90 is generated by computer 80. Next, at step 222, the work product is cut, trimmed or otherwise divided into portions of desired physical parameters, such as weight. Then next, at step 224, the work product can be subjected to one or more further processing operations.

Further Embodiment

FIG. 6 illustrates a further embodiment of the present disclosure wherein the parts or components that operate the same as in FIG. 1 and represented by the same part number, and the components or parts that are similar to these in FIG. 1 are represented by a prime (') designation. In FIG. 6, processing system 10' includes a conveyance system 12' consisting of a first conveyor 100 associated with X-ray scanner 14 and a second conveyor 102 associated with optical scanner 22. Although located apart from each other, X-ray scanner 14 and optical scanner 22 function in the manner described above with respect to portioning system 10.

The first conveyor 100 is operationally and structurally compatible with the X-ray scanner 14. In this regard, the first conveyor 100 includes an X-ray permeable, flat endless belt 104 that is trained over an end roller 106. The endless belt 104 can be powered in a conventional manner. An encoder 108 is associated with the end roller 106 in a manner similar to encoder 20 associated with the roller 34 of conveyor 102. The encoder 108 monitors the location or position of the belt 104 and thus the work product WP, along the length of the conveyor 100.

As mentioned above, the conveyor belt 104 is made from material that is permeable to X-rays, such as rubber, plastic, or a combination of both. Because of this construction, the X-rays easily pass through the conveyor belt to impinge upon the detector 44 located beneath the upper run of the belt 104.

It is to be understood that conveyance devices 12 and 12', as well as other conveyance devices described herein, are not limited to belt conveyors for moving work products either continuously or intermittently. For example, the conveyance devices described herein can be replaced with moving platforms for conveying work products or other conveyance mechanisms.

The X-ray scanner 14, in addition to developing a thickness profile in the manner described above with respect to FIG. 1, also is used to determine other physical parameters of the work product, including the overall shape and size of the work product, the outer perimeter configuration of the work product, as well as the location of the work product on the conveyor belt 104. Such physical parameters are determined by the control system from the data generated by the scanner 14.

After being scanned by X-ray scanner 14 on conveyor 10, the work product is transferred onto a second, downstream conveyor 102. Conveyor 102 is constructed in the manner of conveyor 28 shown in FIG. 1, as described above. As shown in FIG. 6, optical scanner 22 and cutter station 26 are positioned over the downstream conveyor 102. The work product, after being scanned on upstream conveyor 100, is transferred to the downstream conveyor 102 for optical scanning and for processing.

As discussed above, the exterior configuration of the work product is discernible by the optical scanner 22, which ascertains parameters relative to the size and/or shape of the work product, for example, length, width, aspect ratio, thickness, thickness profile, contour (both two-dimensionally and three-dimensionally), outer contour configuration, perimeter, outer perimeter configuration, outer perimeter size and/or shape, volume and/or weight. Thus, the scanner 22 shown in FIG. 6 operates in the same manner as scanner 22 shown in FIG. 1. The data from scanners 14 and 22 shown in FIG. 6 is analyzed in the same manner as described above with respect to FIG. 1 so as to be able to ascertain the existence of and location of voids, undercuts or other anomalies of the work product. Also, as described above, the data from scanners 14 and 22, under certain conditions, can be combined to determine the extent or percentage of fat in meat work products.

Further, as also mentioned above, since the X-ray scanner 14 and optical scanner 22 are located apart from each other, they no longer simultaneously scan the same slice across the work product at the same time. Rather, X-ray scanning of the work product occurs first on the conveyor 100 then optical scanning of the work product occurs on conveyor 102. As also described above, the information from the two scanners must be integrated together or otherwise transformed so that the data from the X-ray scanning corresponds to the same slice taken across the work product as when scanned by the optical scanner 22.

For the foregoing analysis, it is important to verify that the data from the X-ray scanning device corresponds to the same work product as the subsequently obtained data from the optical scanning. In this regard, the control system 18 can identify coordinates along the outer perimeter of the work product as determined by the X-ray scanner and then by the optical scanner, and such data can be compared. If these data sets match within a fixed threshold level, then confirmation is provided that the work product scanned at the optical scanner is the same as the work product previously scanned at the X-ray scanner.

However, if for example, a work product was removed from conveyor 100, or from conveyor 102 before the work product reaches the optical scanner 22, then the next work product scanned at optical scanner 22 will not match the scanning data from the X-ray scanner 14, since the X-ray scanning data will correspond to the work product that has been removed. Thus, the control system 18 will determine that there is no match between the perimeter coordinate data sets of the work products from the X-ray and optical scanners 14 and 22. As such, the optical scanner 22 will scan the next work product which passes by to determine whether such next work product matches the scanning data of the work product scanned at the X-ray scanner 14 and transmitted to the control system 18. The processor will determine whether the work product scanned at the optical scanner 22 corresponds to the work product that was scanned at the X-ray scanner 14 right after the X-ray scanning of the removed work product occurred. The control system 18 will match the correct scanning data from the X-ray scanner 14 with the scanning data from the same work product from the optical scanner 22. Of course, this is essential so that the thickness profile information of the work product determined by the optical scanner 14 coincides with the work product scanned by the optical scanner 22.

The control system 18 will go through the "matching" process a finite number of times. One example of determining the number of data sets from the X-ray scanner that must be checked can be determined as follows. Divide the distance between scanners by the sum of the length of product+ the product gap+a dimensional factor of safety. For example, if there is a disclosure of 9 feet between the X-ray and optical scanners, and the work products are approximately 450 mm long product, then the maximum number of data sets in the queue that will be checked is calculated by: 9*12/(17.7+2+2)=4.9, so five matching attempts are made. The data set from the optical scanner will be compared to five data sets from the X-ray scanner stored in memory unit 82. For longer length products the number of data sets in the memory queue is smaller than for shorter work products. Also, if the distance between the scanners is short enough, only one matching comparison is carried out. Also, it will be appreciated that differences or changes in belt speed can change the number of comparisons that are possible. With faster belt speed, there may need to be a larger gap between products and/or a larger safety margin and there will be less time to make the necessary calculations.

If no match occurs, a "no match found" error message is generated. The system proceeds to the next work product arriving in the optical scanner, and searching for the new work product is initiated.

If for example one work product is removed from the conveyor 100 after the X-ray scanning but before the optical scanning, only two matching attempts should be required before a match occurs. However, in the unlikely event that a work product WP is so distorted in the transfer from belt 104 to belt 30 that the control system 18 fails to recognize the X-ray image of the work product, then after the predetermined matching attempts the work product will proceed down the belt 30 without being cut and/or trimmed/portioned. The above noted error message is generated, and the uncut work product can be identified or marked by the control system 18 and can be removed to a specific location for re-working or other disposition.

It will be appreciated that there is no attempt to continuously track the location of the work product WP from X-ray scanner 14 to optical scanner 22. Rather, the foregoing described methodologies are used to match the work product scanned at X-ray scanner 14 with the same work product scanned at optical scanner 22. Also, although the foregoing description does indicate that the system of the present disclosure can be used to locate the work product on the first and/or second conveyor at one or more specific points in time, the specific location of the work product is not continuously tracked. Moreover, in the present system 10', it is not necessary to locate the work product at any specific time along the conveyance device 12'.

The scanning data from the scanners 14 and 22 can be used to determine whether or not the work product has transferred accurately from conveyor belt 104 to conveyor belt 30 and determine what level of physical distortion or movement of the work product has occurred during the transfer process. Such distortion or movement may include shifting of the work product side-to-side with respect to the center line or other datum line of the conveyors. The work product may also have shifted longitudinally along the length of the conveyor relative to the position of the work product on the conveyor 100.

Figure 7A:
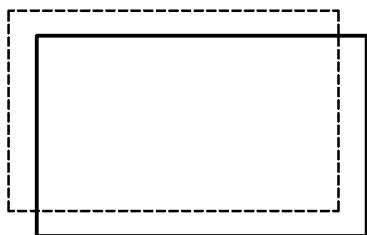
FIGS. 7A-7F schematically illustrate the manner in which work products may move or distort when transferred from a first conveyor belt to a second conveyor belt.

If shifting of the work product occurs in the X and/or Y direction(s), then control system 18 functions to translate or manipulate the X-ray image of the work product and the underlying data from the X-ray imaging to the optically scanned image of the work product so as to improve the match of the shapes or outlines of the work products. This translation is schematically illustrated in FIG. 7A, wherein the work product as scanned at X-ray scanner 14 is shown in broken line and the work product as scanned at optical scanner 22 is shown in solid line. The control system 18 translates the broken line image onto the optical image shown in solid line in FIG. 7A.

Figure 7B:
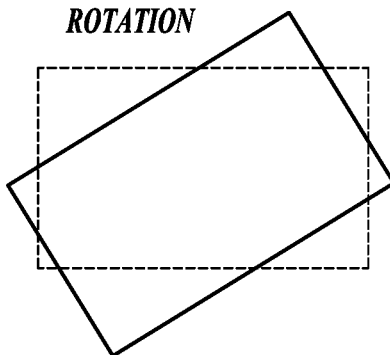

Transfer of the work product from conveyor belt 104 to conveyor belt 30 may also result in rotation of the work product as shown in FIG. 7B, wherein the work product as scanned by X-ray scanner 14 is shown in broken line, whereas the work product as scanned by the optical scanner 22 is shown in solid line. So that the cutter(s) at the cutter station 26 can trim or cut the work product WP, the outline or shape data from the X-ray scanner 14 is transformed onto the image data from the optical scanner 22.

Figure 7C:
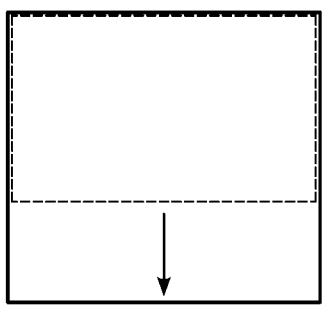
Figure 7D:

A further type of distortion that may occur during transfer of the work product from belt 104 to belt 30 is that the work product may increase or decrease in scale (length) in the Y direction (across belt 30) and/or in the X direction (along belt 30). FIG. 7C shows that the work product has increased in scale in the Y direction, whereas FIG. 7D shows that the work product has increased in scale in the X direction. Of course, the work products may also decrease in scale in the X direction, especially if the scale is increased in the Y direction, and vice versa the work product may decrease in scale in the Y direction especially if increased in scale in the X direction. Nonetheless, the scanning data from the X-ray scanner 14 is transformed in terms of X and Y scale to the work product as scanned by the optical scanner 126.

Figure 7E:

Another form of distortion that may occur during the transfer of the work product from conveyor belt 104 to conveyor belt 30 is a distortion in shear in the X direction, as shown in FIG. 7E. In shear distortion, the work product may progressively distort or shift in the X direction across the width of the work product as shown in FIG. 7E. Of course, the shear distortion may occur as a mirror image as that shown in FIG. 7E. Also, the shear distortion is shown as occurring progressively linearly across the work product, but the shear distortion also may be non-linear across the work product. As with other types of distortion, shear distortion may be due to various causes, such as a difference in the speeds of the conveyors or imperfect alignment of the two conveyors. As a result, in the direction across the conveyor belt, the work product may have progressively shifted rearwardly or forwardly relative to the direction of travel of the conveyor belt.

FIG. 7E shows a forward (in the right-hand direction) shifting of the work product on the second conveyor belt 30 due to shear distortion. As noted above, of course the shear distortion could have occurred in the opposite direction (in the left-hand direction) so that the work product extends rearwardly relative to the nominal position of the work product going across the conveyor belt.

Figure 7F:
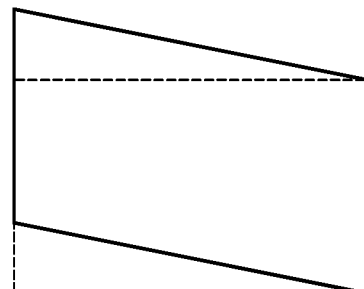

FIG. 7F illustrates that shear distortion can occur in the Y direction, wherein the work product shifts laterally relative to the belt along the length of the work product. FIG. 7F shows shear distortion of the work product in the Y direction (upward along the page). It will be appreciated that the shear distortion may occur in the opposite direction than as shown in FIG. 7F.

Regardless of the direction of the shear distortion, the data from the X-ray scanner is transformed onto the work product as scanned at the optical scanner. Once the needed transformations have occurred to correct for movement and/or distortion of the work products, the shape, size, and outline of the work product from the optical scanner has been better matched to the position, orientation, and/or shape of the work product as scanned by the optical scanner.

It will be appreciated that without the foregoing transformation step or steps to correct or adjust for the distortion and/or shifting that may have occurred to the work product during transfer from conveyor 100 to conveyor 102, the determination of the thickness and thickness profile of the work product may be erroneous. As such attempts to determine the location of voids, undercuts and other anomalies in the work product may prove unsuccessful.

As with the "matching" analysis described above to verify that the work product optically scanned at optical scanner 22 is the same work product that was previously scanned at X-ray scanner 14, the data sets analyzed by the control system 18 to perform the above transformations may consist of coordinate locations along the outer perimeter of the work product. In this regard, the control system 18 may compare the data consisting of coordinate locations along the outer perimeter of the work product as determined at the X-ray scanner 14 with the corresponding coordinates of the same locations along the outer perimeter of the work product as determined at the optical scanner 22. Such comparison of the data sets can be used to determine whether or not the work product upon transfer to the conveyor belt 20 has distorted or shifted, for example, in X-Y translation, rotation about the Z axis. Mismatch of the data sets will indicate what type(s) of distortion occurred and the extent of such distortion so that an appropriate correcting transformation of the X-Y scanning data can be applied to the work product as scanned by the optical scanner 22.

Once the work product has passed the optical scanner 22, it moves on to the cutting station 26. As described above, the information from the X-ray scanner and the optical scanner are combined so that the location of voids, undercuts and other anomalies can be determined.

Method

Figure 8:
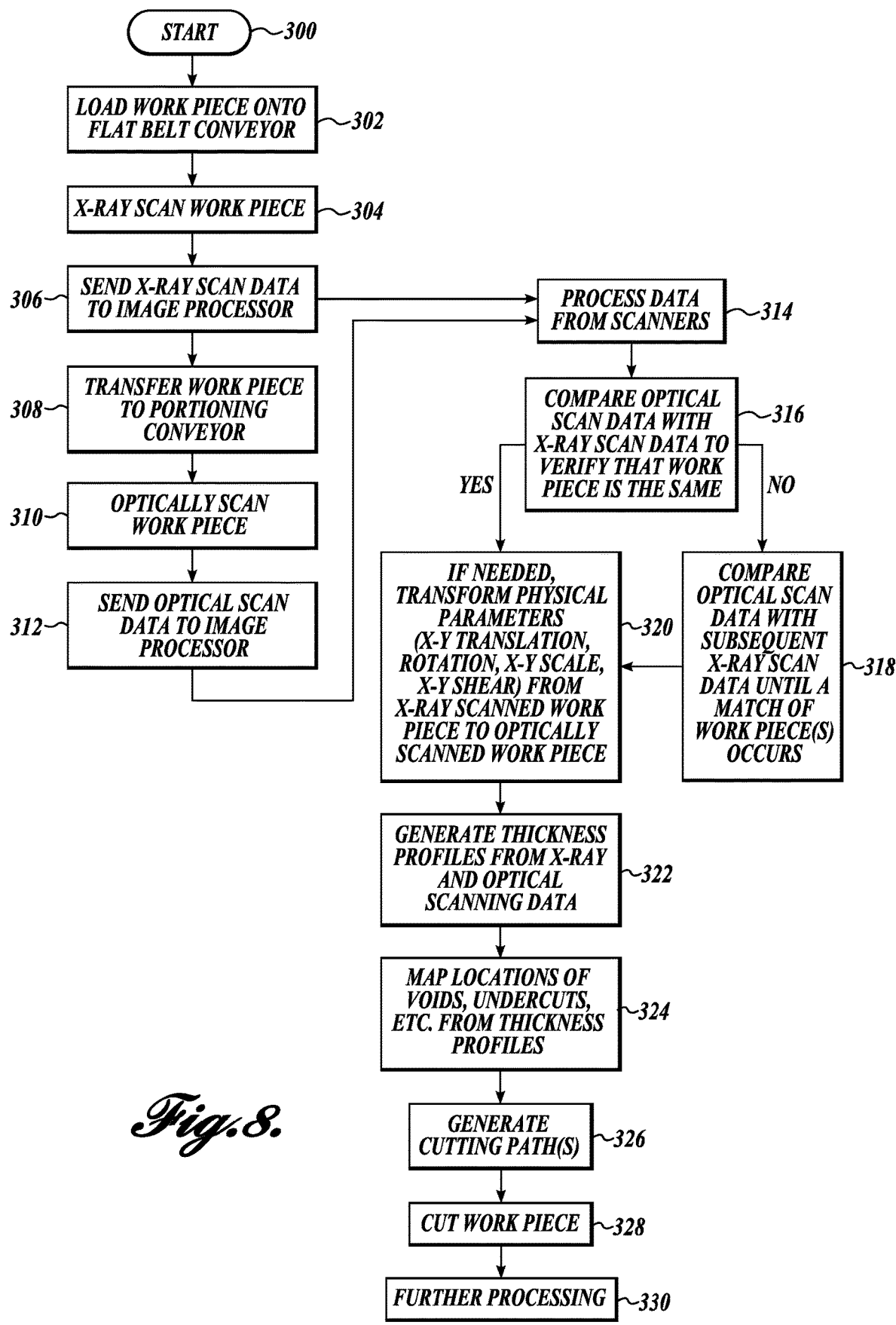
FIG. 8 is a flow diagram illustrating one method of utilizing the system and apparatus of FIG. 6.

A method of utilizing the processing system 10' of the present disclosure is schematically illustrated in FIG. 8. The process begins at step 300 wherein work products are loaded onto flat belt conveyor 100 at step 302. Thereafter, the work products are scanned using X-ray scanner 14 at step 304. Next, at step 306, the data from the scanning of the work product is transmitted to image processor 46.

Next, at step 308, the work product is transferred from the X-ray scanning conveyor 100 to the portioning conveyor 102. Thereafter, at step 310, the work product is optically scanned by scanner 22. Thereafter at step 312, the data generated by the optical scanner 22 is transmitted to the image processor 46, see step 312.

Next, at step 316, computer 80 compares the output from the image processor 46 to determine whether or not the work product being optically scanned is the same as that which was previously scanned by the X-ray scanner. As discussed above, the data being compared can consist of coordinate locations along the outer perimeter of the work product.

Various methods and techniques can be used to compare the first data set from the X-ray scanner 14 with the second data set from the optical scanner 22 to verify that the work product scanned by the optical scanner corresponds to the same work product previously scanned by the X-ray scanner. For example, the Root Mean Square (RMS) error between the two data sets can be calculated and such error value compared with the maximum RMS previously established for verifying that the food item scanned by the X-ray scanner is the same as the food item scanned by the optical scanner. In this regard, an RMS error is calculated for each corresponding coordinate locations along the outer perimeter of the work product. In essence, the difference in position of each of the coordinates is calculated as the root square of the sum of the squares of the difference in X and Y coordinate values. Thereafter, the square values of these distances are summed up, and the sum is divided by the number of corresponding coordinate pairs. Finally, the square root of the quotient is taken as an RMS error. The calculated RMS error is compared with the pre-established maximum RMS error allowable and still concluding that the same work product was scanned by the optical scanner and the X-ray scanner.

Another analysis methodology that may be utilized is by determining the difference in the X and Y coordinate values of each location along the work product and selecting a standard deviation that defines an acceptable variation or difference in the X-Y coordinate values. In this technique, a confidence level may be defined in terms of the standard deviation at each of the various coordinate locations along the perimeter of the work product. An acceptable confidence level or level of allowable standard deviation between the X-Y coordinate is established ahead of time.

Other regression analysis techniques may also be utilized, for example the least squares regression analysis.

If it is determined that the work product from the optical scan matches that of the previous X-ray scan, then at step 320, the control system 18 proceeds to determine if there is a need to transform physical parameter data from the X-ray scanning results to the optical scanning results due to movement or distortion of the work product when transferred to the portioning conveyor 102. As discussed above, such distortion may include X and/or Y translation of the work product, rotation of the work product about the Z axis, change in scale of the work product in the X and/or Y directions, and shear distortion in the X and/or Y directions. If sufficient shifting or distortion in the work product WP has occurred, then the requisite transformations are carried out by the processor 18. As a result, a close match is achieved between the configuration, including, for example, outer perimeter and size and shape of the work product as scanned by the X-ray scanner 14 and optically scanned by the optical scanner 22.

If, on the other hand, it is determined that the work product WP from the optical scan does not match that of the previous X-ray scan, then the processor at step 318 compares the optically scanned data with the next data set received from the X-ray scanning to determine whether the next work product on the conveyor belt is the same as the work product from the optical scan. In this situation, if a single work product was removed from either first conveyor 100 or second conveyor 102 at a location upstream from the optical scanner 14, then the next work product traveling along the conveyors will correspond to the work product which was optically scanned. However, if more than one work product WP was removed from the conveyors upstream from optical scanner 22, then the computer 80 continues with the comparison analysis until a match occurs between the work product, which has been optically scanned, and the corresponding work product which has been scanned at X-ray scanner. Once a match has been achieved in the data sets from the X-ray scanning and the optical scanning, then the process moves to step 320 to determine if there is a need to carry out any transformations as discussed above.

Next, at step 322, the thickness profiles of the work product are generated from the X-ray and optical scanning data. Thereafter, at step 324 the thickness profiles from the X-ray scanning data and the optical scanning data are analyzed for the presence of undercuts, voids and other anomalies in the work product, and if undercuts, voids or anomalies exist, then the location, size and shape of such are mapped at step 324.

Thereafter, the cutting path or paths for cutter 90 is generated at step 326 bearing in mind the result of the analysis at prior step 324. Next, at step 328, the work product is trimmed, cut, or otherwise portioned in the manner determined at step 326. Next, at step 330, the work product can be subjected to one or more further processing operations.

Further Embodiment

Figure 9:
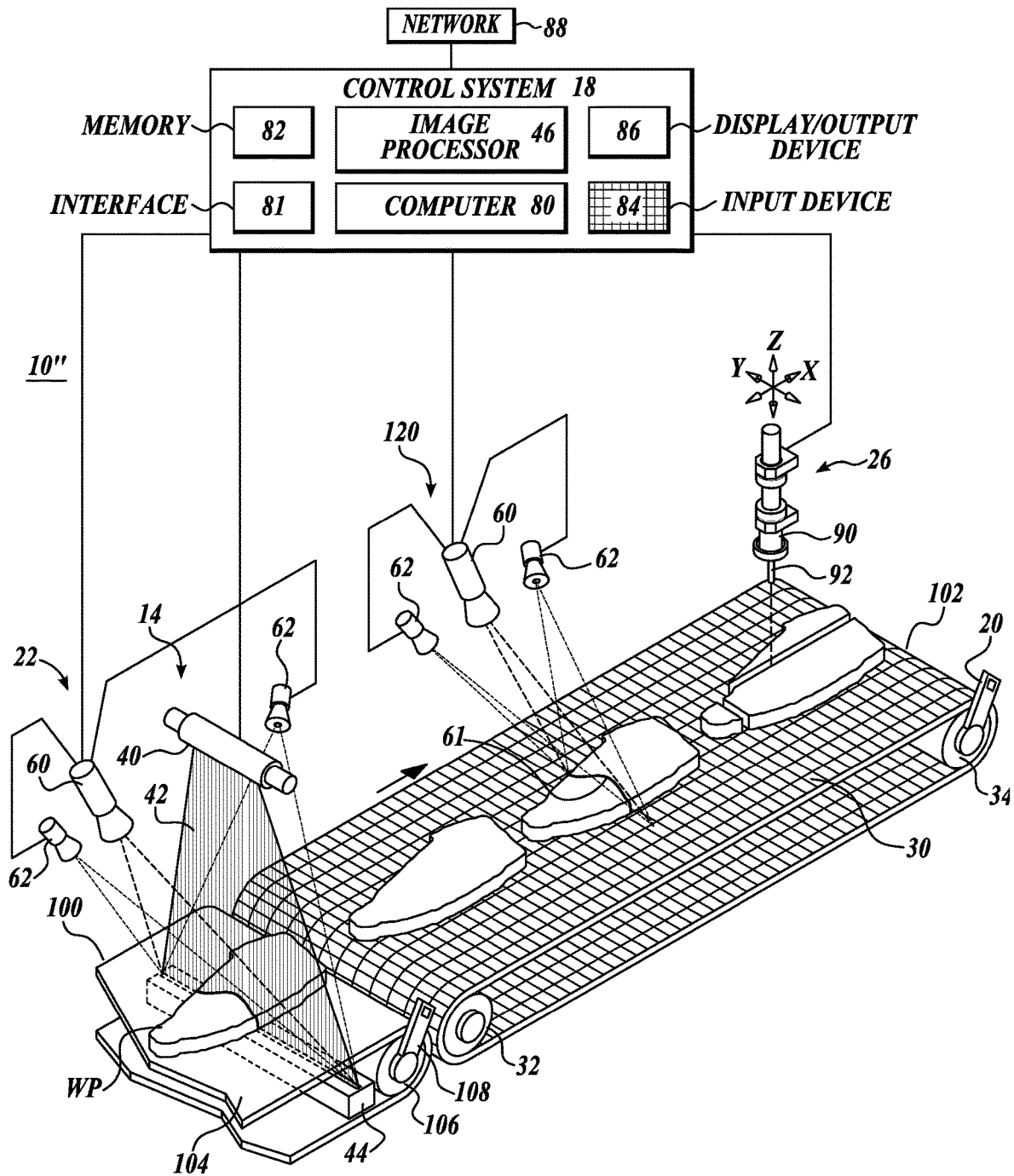
FIG. 9 is a schematic view of another embodiment of a system and apparatus for processing work products in accordance with the present disclosure.
Figure 10:
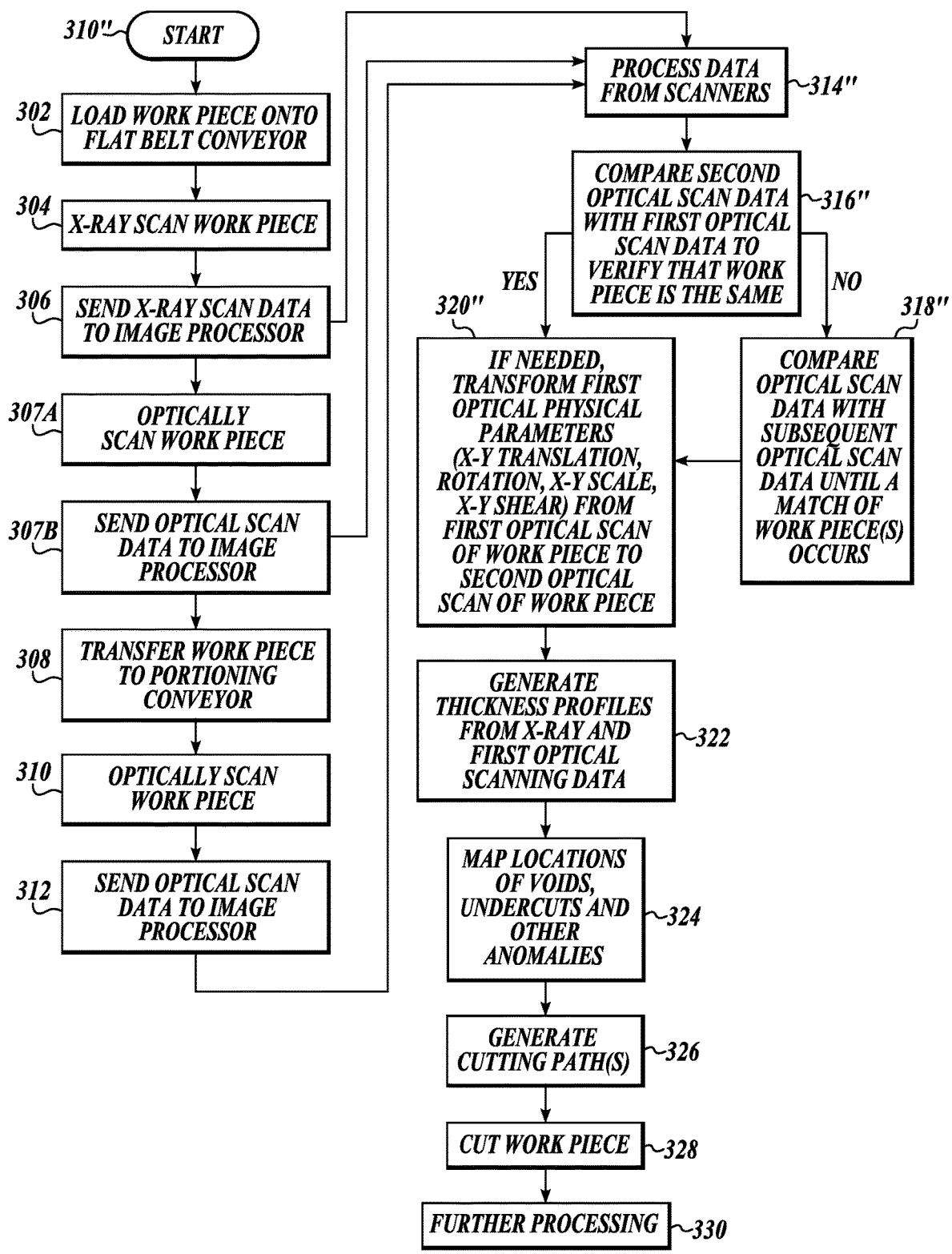
FIG. 10 is a flow diagram schematically illustrating a method of utilizing the system and apparatus of FIG. 9.

FIGS. 9 and 10 illustrate a further processing system 10" and method in accordance with the present disclosure. The components and parts of system 10" shown in FIG. 9 that are the same as in FIGS. 1-4 and 6 are identified with the same reference numbers, and their descriptions will not be repeated here. Rather, the following description will focus on the changes or differences in the system 10" and the method as shown in FIGS. 9 and 10 relative to that illustrated in FIGS. 1-8. Nonetheless, it is to be understood that applicable components and parts of system 10" do apply to the embodiment of FIG. 1. The same pertains to the steps of FIG. 5.

Referring to FIG. 9, the portioning system 10" includes X-ray scanner 14 and optical scanner 22 in the same manner as shown in FIG. 1 except located over a smooth X-ray pervious belt 100' rather than over the open weave belt 30 shown in FIG. 1. Further, the system 10" shown in FIG. 9 includes a second optical scanner 120 located over the belt 30 of second conveyor 102". Although the optical scanner 120 is illustrated as being of substantially the same construction as scanner 22, other types of optical scanners could be used for both optical scanner 22" and 120. For example, these optical scanners can utilize charged coupled devices (CCD) or infrared cameras.

One difference in system 10" versus system 10' is that the X-ray scanner 14 need not be used to determine the outer contours of the work product and then such data translated into the data from optical scanner 120 located above conveyor 102'. Rather, the data pertaining to the outer contour of the work product can be obtained from the optical scanner 22 located above the first conveyor 100' and such data pertaining to the outer contour of the work product can be compared with corresponding data obtained from downstream optical scanner 120. Thus, the type of data being generated with respect to determining the outer contour of the work product is of the same nature thereby reducing the complexity of comparing the two data sets from the two optical scanners 22 and 120.

Other than as just described, the processing apparatus 10" shown in FIG. 9 is the same as the processing system 10' shown in FIG. 6. Moreover, since the imaging process of the two optical scanners 120 and 22 are the same, a better match between the data from the two optical scanners may occur than when using data from X-ray scanner 14 and optical scanner 22 in seeking to confirm that the same work product is being scanned by the optical scanner 22 as previously scanned by the X-ray scanner 14 as well as when seeking to determine whether the work product has moved to such an extent during transfer from the upstream smooth belt conveyor to the downstream portioning conveyor that the data pertaining to the physical parameters of the work product from the upstream scanner must be transformed with respect to the data obtained from the downstream scanning Method The method of utilizing the processing system 10" of the present disclosure is schematically illustrated in FIG. 10. To a large extent, the method shown in FIG. 10 is the same as shown in FIG. 8, with the differences primarily due to the use in a system 10" of a second optical scanner 120 positioned over the portioning conveyor 102. Accordingly, the steps in FIG. 10 that are the same as in FIG. 8 are indicated with the same part numbers, and the steps that are similar to the steps of FIG. 8 are indicated by use of a double prime (") after the number of the step. As such, the following description will focus on the differences between a method in FIG. 10 versus the method in FIG. 8.

With respect to the method of FIG. 10, in step 307a the work product is optically scanned simultaneously with the X-ray scanning, and at the same location across the work product, for example, as shown above in FIG. 1 and discussed in the method illustrated in FIG. 5. In step 307b, the first optical scanner data is sent to image processor 46.

At step 314", the data from the X-ray scanning and both optical scanners is processed by the image processor 46. Then at step 316", the optical scanner data from the scanner 112 is compared with the data from the scanner 14 to verify that the work product is the same. If not, then the process moves to step 318" in the same manner as described above, but in the present situation using data from the two optical scanners rather than data from an X-ray scanner and an optical scanner. Further, at step 320 a determination is made if transformation of the data from the first optical scanner 14 needs to be integrated into the data from the second optical scanner 120 due to movement or distortion of the work product when transferred from conveyor 100 to conveyor 102. Other than these steps, the process shown in FIG. 10 coincides to the process shown in FIG. 8.

While illustrative embodiments have been illustrated and described, it will be appreciated that various changes can be made therein without departing from the spirit and scope of the invention. For example, the foregoing describes X-ray scanning occurring prior to optical scanning or that X-ray and optical scanning occur at the same time. It is to be understood that the present disclosure also envisions optical scanning occurring ahead of X-ray scanning and then the data from both optical and X-ray scanning being analyzed to determine the presence of voids, undercuts and similar anomalies due to the differences in the thickness profile of the work product as determined by analysis of the data from the optical scanning and X-ray scanning.

As another embodiment of the present disclosure, it is contemplated that in some situations similar to that of FIG. 9, the transfer of the work product from conveyor 100 to conveyor 102 may occur accurately enough that a second optical scanner, such as scanner 120, is not needed. In this situation, small diameter end rollers at each end of the conveyor may be use at the interface of conveyors 100 and 102. Or a transfer conveyor having small diameter end rollers may be used to bridge between conveyors 100 and 102. As such, the processing of the work product can occur on conveyor 102 without the need for the second scanner 120. See, for example, US Publication No. 2018/0029246, which is incorporated by reference herein. This could simplify the processing system and method and also enable faster throughput of the work products.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for determining the thickness profile of a work product, comprising:
    a. scanning a work product with an X-ray scanner,
    b. analyzing the data from the X-ray scanner with a computer processor to develop a thickness profile of the work product,
    c. scanning the work product with an optical scanner,
    d. analyzing the data from the optical scanner with a computer processor to develop a thickness profile of the work product based on the optical scanning data,
    e. comparing the thickness profiles from the X-ray scanning data and the optical scanning data and determining (quantifying) the differences between the thickness profiles from the X-ray scanning data and the optical scanning data, and
    f. mapping the location(s) on the work product where a difference exists between the thickness profiles from the X-ray scanning data and the optical scanning data.

2. The method of claim 1, wherein the work product is a food product, and the differences between the thickness profile developed from the X-ray scanning data and the thickness profile developed from the optical scanning data correspond to: a void in the work product; an undercut beneath the work product; or other location devoid of the work product.

3. The method of claim 1, further comprising transporting the work product on a conveyance device past the X-ray scanner and the optical scanner.

4. The method of claim 1, further comprising positioning the X-ray scanner and the optical scanner relative to the conveyance device to simultaneously scan the same location on the work product.

5. The method of claim 1, further comprising processing the work product using the determined differences between the thickness profiles from the X-ray scanning data and the optical scanning data and the location(s) on the work product where a difference exists between the thickness profiles from the X-ray scanning data and the optical scanning data.

6. The method of claim 1, further comprising:
    transporting the work product in a direction of travel past the X-ray scanner and the optical scanner;
    wherein the X-ray scanner scans the work product along a line extending transversely to the direction of travel of the work product and
    wherein the optical scanner scans the work product along a line extending transversely to the direction of travel of the work product.

7. The method of claim 6, further comprising transporting the work product past the X-ray scanner on a first conveyor and transporting the work product past the optical scanner on a second conveyor.

8. The method of claim 7, further comprising:
g. wherein the data from the X-ray scanning comprises a first data set corresponding to the two dimensional shape of the work product,
h. wherein the data set from the optical scanning comprises a second data set corresponding to the two dimensional shape of the work product,
i. comparing the first and second data sets from the X-ray scanning and the optical scanning corresponding to the two-dimensional shape of the work product, and
j. determining if a sufficient variation exists between the first and second data sets to require translation of the first data set into the second data set.

9. The method of claim 8, wherein translation of the first data set from the X-ray scanning onto the second data set from the optical scanning comprises one or more of:
(i) directional translation of the work product;
(ii) rotational translation of the work product;
(iii) scaling the size of the work product;
(iv) shear distortion of the work product.

10. The method of claim 6, further comprising transporting the work product past the X-ray scanner and the optical scanner on a first conveyor and transporting the work product to a processing station on a second conveyor whereat the work product is processed using the thickness profiles determined from the X-ray scanning data and the optical scanning data.

11. A system for determining the thickness profile of a work product, comprising:
a conveyance device for conveying the work product;
an X-ray scanner for scanning the work product being conveyed on the conveyance device and generating a first data set regarding the physical characteristics of the work product, including a thickness profile of the work product;
an optical scanner for scanning the work product being conveyed on the conveyance device for generating a second data set regarding the physical characteristics of the work product, including the thickness profile of the work product; and
a control system configured to:
generating thickness profiles of the work product from the X-ray scanning data and the optical scanning data;
quantifying the differences between the thickness profiles of the work product from the X-ray scanning data and the optical scanning data; and
mapping the location(s) on the work product where differences exist between the thickness profiles from the X-ray scanning data and the optical scanning data.

12. The system according to claim 11, wherein the work product comprises a food product and the differences between the thickness profile of the food product from the X-ray scanning data and the thickness profile of the food product from the optical scanning data corresponds to a void in the food product, an undercut beneath the food product, or location with respect to the food product that is devoid of the food product.

13. The system according to claim 11, wherein the X-ray scanner and the optical scanner are positioned relative to the conveyance device to simultaneously scan the same location on the work product.

14. The system according to claim 11, wherein:
the X-ray scanner is configured to scan the work product along a line extending transversely to the direction of travel of the work product on the conveyance device; and
the optical scanner is configured to scan the work product along a line extending transversely to the direction of travel of the work product on the conveyance device.

15. The system according to claim 14, wherein the optical scanner is configured to scan the work product along the same line that the X-ray scanner is configured to scan the work product.

16. The system according to claim 15, wherein the optical scanner is configured to scan the work product along the same line and at the same time that the X-ray scanner is configured to scan the work product.

17. The system according to claim 11, wherein the conveyance device comprises a first conveyor corresponding to the X-ray scanner and a second conveyor corresponding to the optical scanner.

18. The system according to claim 17, wherein the control system compares a first data set from the X-ray scanning data corresponding to the two-dimensional shape of the work product with a second data set from the optical data scanning corresponding to the two-dimensional shape of the work product and comparing the first and second data sets from the X-ray scanning and the optical scanning to determine if a sufficient variation exists between the first and second data sets to require translation of the first data set into the second data set.

19. The system according to claim 18, wherein the translation of the first data set from the X-ray scanning into the second data set from the optical scanning comprises one or more of:
directional translation of the work product;
rotational translation of the work product;
scaling of the size of the work product; and
shear distortion of the work product.

20. The system according to claim 11, further comprising a processing station located downstream of the optical scanner for processing the work product using the quantified differences between the thickness profile of the work product from the X-ray scanning versus the thickness profile of the work product from the optical scanning.

* * * * *